United States Patent
Hara et al.

(10) Patent No.: US 11,547,541 B2
(45) Date of Patent: Jan. 10, 2023

(54) DENTAL CEMENT KIT

(71) Applicant: SHOFU INC., Kyoto (JP)

(72) Inventors: Daisuke Hara, Kyoto (JP); Naoya Kitada, Kyoto (JP); Kenzo Yamamoto, Kyoto (JP); Yasuhiro Nishino, Kyoto (JP); Yoshiyuki Jogetsu, Kyoto (JP)

(73) Assignee: SHOFU INC., Kyoto (JP)

( * ) Notice: Subject to any disclaimer, the term of this patent is extended or adjusted under 35 U.S.C. 154(b) by 730 days.

(21) Appl. No.: 16/575,867

(22) Filed: Sep. 19, 2019

(65) Prior Publication Data

US 2020/0214819 A1 Jul. 9, 2020

(30) Foreign Application Priority Data

Sep. 20, 2018 (JP) .............. JP2018-175604

(51) Int. Cl.
| | |
|---|---|
| *G01J 3/00* | (2006.01) |
| *A61C 19/10* | (2006.01) |
| *A61K 6/849* | (2020.01) |
| *A61K 6/15* | (2020.01) |
| *A61K 6/30* | (2020.01) |
| *A61K 6/78* | (2020.01) |

(52) U.S. Cl.
CPC .............. *A61C 19/10* (2013.01); *A61K 6/849* (2020.01); *G01J 3/00* (2013.01); *A61K 6/15* (2020.01); *A61K 6/30* (2020.01); *A61K 6/78* (2020.01)

(58) Field of Classification Search
CPC ......... A61C 19/10; A61C 13/082; A61C 5/20; A61K 6/849; A61K 6/15; A61K 6/30; A61K 6/78; G01J 3/00; G06T 5/007; G06T 7/90
See application file for complete search history.

(56) References Cited

U.S. PATENT DOCUMENTS

| | | | |
|---|---|---|---|
| 4,678,436 A * | 7/1987 | Kondo ..................... | A61K 6/30 106/35 |
| 2002/0064749 A1 * | 5/2002 | Didier ..................... | G01J 3/508 433/26 |

* cited by examiner

*Primary Examiner* — Abdullahi Nur
(74) *Attorney, Agent, or Firm* — Wenderoth, Lind & Ponack, L.L.P.

(57) ABSTRACT

[Problem]
To select a dental cement or a trial test material for easily obtaining high color tone adaptability to peripheral tooth substances, in mounting of or trial test of a prosthesis device
[Solution]
To provide a dental cement set consisting of a plurality of dental cements having color tones including color tones of 3 to n colors for selecting and using a dental cement from the plurality of dental cements having the color tones including the color tones of the 3 to n colors after trial test with trial test materials for the dental cement to be used from the plurality of dental cements having the color tones including the color tones of the 3 to n colors, wherein:

the amount of information loss Pin with regard to first principal component determined by principal component analysis is less than 2, and.

the dental cement set satisfies following Formula 1.

$$2 \leq ((CL^*_{p-1} - CL^*_p)^2 + (Ca^*_{p-1} - Ca^*_p)^2 + (Cb^*_{p-1} - Cb^*_p)^2)^{1/2} < 8 \quad \text{Formula 1}$$

(wherein p is an arbitrary integer of $2 \leq p \leq n$).

8 Claims, 2 Drawing Sheets

DENTAL CEMENT KIT

CROSS-REFERENCE TO RELATED APPLICATIONS

This application is based on and claims the benefit of priority from Japanese Patent Application Serial No. 2018-175604 (filed on Sep. 20, 2018), the contents of which are hereby incorporated by reference in their entirety.

BACKGROUND OF THE INVENTION

Field of the Invention

The present invention relates to a dental cement selection method selecting a dental cement to be used from a plurality of dental cements having color tones including color tones of 3 to n colors after trial test with a plurality of trial test materials corresponding to the color tone of each dental cement in the field of dental treatment, the dental cement, the trial test material and the kit thereof.

Description of the Related Art

In late years, the center of prosthesis restoration has changed from metal prosthesis restoration using metal as main material to aesthetic prosthesis restoration using prosthesis devices of ceramics or hybrid ceramic materials.

The aesthetic prosthesis restoration is a restoration method in which restoration of aesthetic property as well as restoration of functionality such as the occlusion can be expected by mounting a prosthesis device having color tone and optical characteristics (opal effect, fluorescent property, transparency and the like) like the natural tooth and adapting the color tone to peripheral tooth substances such as an adjacent tooth and a remaining tooth substance.

An explanation of flow the general aesthetic prosthesis restoration will be described. An impression of the portion needing restoration of aesthetic property and functionality by caries removal or twisting is taken, a dental technician prepares a model using the impression body and a prosthesis device which adapts the model is prepared while considering the color tone of peripheral tooth substances. Then, a dentist confirms adaptability of a form and a color of the prosthesis device by a trial test of mounting the prosthesis device on a tooth. In the present invention, the trial test means a work of confirming adaptability of a form and a color by using a dental color tone adaptability confirming material which can be easily removed from a tooth and can reproduce the color tone of dental cement after curing (herein after referred "trial test material"), instead of dental cement. As well as functionality, aesthetic property can be restored by mounting on the tooth by using a dental cement having the same color tone as that of the trial test material after confirming adaptability of a form and a color.

In preparing a prosthesis device, a dental technician is required to reproduce aesthetic property like a natural tooth by imparting a three-dimensional color tone to the prosthesis device while considering the brightness (L* value by the L*a*b* color system), the saturation (a* value and b* value by the L*a*b* color system) and the surface structure of peripheral tooth substances.

However, because color tone adjustment of the prosthesis devise is performed based on an oral cavity photograph taken by a dentist or shade (color tone) information visually determined by a dentist, when the mounting of or the trial test of the actually prepared prosthesis device in an oral cavity is performed, there is a case that a slight color difference is generated between a portion to be restored and peripheral tooth substances. When the color tone adaptability of the prosthesis device clearly differs from the peripheral tooth substances, it is necessary to perform re-preparing or color tone adjustment of the prosthesis device. However, when the color tone adaptability of the prosthesis device slightly differs from the peripheral tooth substances, it is possible to amend by color tone of a dental cement or a trial test material. For example, when a portion to be restored is darker than peripheral tooth substances, it is possible to improve adaptability to the color tone of peripheral tooth substances by using a dental cement or a trial test material having higher brightness than the peripheral tooth substances. Similarly, it is possible to amend saturation by a dental cement or a trial test material, for example, when redness of a portion to be restored is short in comparison with peripheral tooth substances, it is possible to improve adaptability to the color tone of peripheral tooth substances by using a dental cement or a trial test material having more stronger redness than the peripheral tooth substances.

However, it was difficult to adjust the color in a portion to be restored by the conventional dental cement or a trial material as shown in a non-patent literature 1, for example. This is caused by that color differences between each two color tones (distance between each c two color tones in the L*a*b* space) are not in a constant interval and each color tone is dispersed in the L*a*b* space. Therefore, because it was necessary for the dentist to repeat the trial test work based on a color sample or shade guide of dental cements, or to select color tone based on experimental rule, it has not been easy to obtain high color tone adaptability to peripheral tooth substances.

RELEVANT REFERENCES

Non-Patent Literature

[Non-Patent Literature 1] PANAVIA V5 Try-in Paste (Kuraray Noritake Dental INC.) <URL:https://www.kuraraynoritake.jp/product/cements/pdf/panaviav5_catalog.pdf>

SUMMARY OF THE INVENTION

Technical Problem

Is has been difficult to select a dental cement or a trial test material for easily obtaining high color tone adaptability to peripheral tooth substances in mounting of or trial test of a prosthesis device.

Solution to Problem

The dental cement set of the present invention is a dental cement set consisting of a plurality of dental cements having color tones including color tones of 3 to n colors for selecting and using a dental cement from the plurality of dental cements having the color tones including the color tones of the 3 to n colors after trial test with trial test materials for the dental cement to be used from the plurality of dental cements having the color tones including the color tones of the 3 to n colors, wherein:

when it is defined that $C_1$ ($CL^*_1$, $Ca^*_1$, $Cb^*_1$) is a color tone having higher L* value in two color tones having the longest distance, and $C_2$ ($CL^*_2$, $Ca^*_2$, $Cb^*_2$), $C_3$ ($CL^*_3$, $Ca^*_3$, $Cb^*_3$), to $C_{n-1}$, ($CL^*_{n-1}$, $Ca^*_{n-1}$, $Cb^*_{n-1}$), Cn ($CL^*_n$, $Ca^*_n$, $Cb^*_n$) are color tones in the order of closer distance from the $C_1$ ($CL^*_1$, $Ca^*_1$, $Cb^*_1$), in the $L^*a^*b^*$ space, each color tone C ($CL^*$, $Ca^*$, $Cb^*$) in the plurality of dental cements having the 3 to n colors satisfies that an amount of information loss Pin in each color tone with regard to first principal component determined by principal component analysis of each of the color tones $C_1$ ($CL^*_1$, $Ca^*_1$, $Cb^*_1$), $C_2$ ($CL^*_2$, $Ca^*_2$, $Cb^*_2$), to $C_{n-1}$, ($CL^*_{n-1}$, $Ca^*_{n-1}$, $Cb^*_{n-1}$), Cn ($CL^*_n$, $Ca^*_n$, $Cb^*_n$) is less than 2, and following Formula 1.

$$2 \le ((CL^*_{p-1} - CL^*_p)^2 + (Ca^*_{p-1} - Ca^*_p)^2 + (Cb^*_{p-1} - Cb^*_p)^2)^{1/2} < 8 \quad \text{Formula 1}$$

(wherein p is an arbitrary integer of $2 \le p \le n$)

In the dental cement set of the present invention, it is preferable that the amount of information loss Pin with regard to the first principal component which is determined by the principal component analysis is less than L5.

The dental cement trial test material kit of the present invention is a dental cement trial test material kit comprising the dental cement set of the present invention and a trial test material set consisting of a plurality of trial test materials corresponding to the color tone of each dental cement, wherein, each color tone $T_1$ ($TL^*_1$, $Ta^*_1$, $Tb^*_1$), $T_2$ ($TL^*_2$, $Ta^*_2$, $Tb^*_2$), to $T_{n-1}$, ($TL^*_{n-1}$, $Ta^*_{n-1}$, $Tb^*_{n-1}$), Tn ($TL^*_n$, $Ta^*_n$, $Tb^*_n$) of the trial test materials corresponding to each color tone $C_1$ ($CL^*_1$, $Ca^*_1$, $Cb^*_1$), $C_2$ ($CL^*_2$, $Ca^*_2$, $Cb^*_2$), to $C_{n-1}$, ($CL^*_{n-1}$, $Ca^*_{n-1}$, $Cb^*_{n-1}$), Cn ($CL^*_n$, $Ca^*_n$, $Cb^*_n$) of the dental cements having the 3 to n colors in $L^*a^*b^*$ space satisfies following Formula 2.

$$0 \le ((CL^*_p - TL^*_p)^2 + (Ca^*_p - Ta^*_p)^2 + (Cb^*_p - Tb^*_p)^2)^{1/2} \le 2, \text{ and } 0 \le ((CL^*_1 - TL^*_1)^2 + (Ca^*_1 - Ta^*_1)^2 + (Cb^*_1 - Tb^*_1)^2)^{1/2} \le 2 \quad \text{Formula 2}$$

(wherein p is an arbitrary integer of $2 \le p \le n$).

The dental cement selection method of the present invention is a dental cement selection method selecting a dental cement to be used from a plurality of dental cements having color tones including color tones of 3 to n colors after trial test with a plurality of trial test materials including trial test materials corresponding to the color tones of the 3 to n colors, wherein the method uses a dental cement trial test material kit comprising a dental cement set and a trial test material set, wherein:

the dental cement set consisting of a plurality of dental cements having color tones including color tones of 3 to n colors, wherein when it is defined that $C_1$ ($CL^*_1$, $Ca^*_1$, $Cb^*_1$) is a color tone having higher $L^*$ value in two color tones having the longest distance, and $C_2$ ($CL^*_2$, $Ca^*_2$, $Cb^*_2$), $C_3$ ($CL^*_3$, $Ca^*_3$, $Cb^*_3$), to $C_{n-1}$, ($CL^*_{n-1}$, $Ca^*_{n-1}$, $Cb^*_{n-1}$), Cn ($CL^*_n$, $Ca^*_n$, $Cb^*_n$) are color tones in the order of closer distance from the $C_1$ ($CL^*_1$, $Ca^*_1$, $Cb^*_1$), in the $L^*a^*b^*$ space, each color tone C ($CL^*$, $Ca^*$, $Cb^*$) in the plurality of dental cements having the 3 to n colors satisfies that an amount of information loss Pin in each color tone with regard to first principal component determined by principal component analysis of each of the color tones $C_1$ ($CL^*_1$, $Ca^*_1$, $Cb^*_1$), $C_2$ ($CL^*_2$, $Ca^*_2$, $Cb^*_2$), to $C_{n-1}$, ($CL^*_{n-1}$, $Ca^*_{n-1}$, $Cb^*_{n-1}$), Cn ($CL^*_n$, $Ca^*_n$, $Cb^*_n$) is less than 2, and following Formula 1, $$2 \le ((CL^*_{p-1} - CL^*_p)^2 + (Ca^*_{p-1} - Ca^*_p)^2 + (Cb^*_{p-1} - Cb^*_p)^2)^{1/2} < 8 \quad \text{Formula 1}$$

(wherein p is an arbitrary integer of $2 \le p \le n$), and the trial test material set consisting of a plurality of trial test materials corresponding to the color tone of each dental cement, wherein, each color tone $T_1$ ($TL^*_1$, $Ta^*_1$, $Tb^*_1$), $T_2$ ($TL^*_2$, $Ta^*_2$, $Tb^*_2$), to $T_{n-1}$, ($TL^*_{n-1}$, $Ta^*_{n-1}$, $Tb^*_{n-1}$), Tn ($TL^*_n$, $Ta^*_n$, $Tb^*_n$) of the trial test materials corresponding to each color tone of the dental cements having the 3 to n colors satisfies following Formula 2.

$$0 \le ((CL^*_p - TL^*_p)^2 + (Ca^*_p - Ta^*_p)^2 + (Cb^*_p - Tb^*_p)^2)^{1/2} \le 2, \text{ and } 0 \le ((CL^*_1 - TL^*_1)^2 + (Ca^*_1 - Ta^*_1)^2 + (Cb^*_1 - Tb^*_1)^2)^{1/2} \le 2 \quad \text{Formula 2}$$

(wherein p is an arbitrary integer of $2 \le p \le n$).

The dental cement set of the present invention is a dental cement set consisting of a plurality of dental cements having color tones of 3 to n colors for selecting and using a dental cement from the plurality of dental cements having the color tones of the 3 to n colors after trial test with trial test materials for the dental cement to be used from the plurality of dental cements having the color tones including the color tones of the 3 to n colors, wherein:

when it is defined that $C_1$ ($CL^*_1$, $Ca^*_1$, $Cb^*_1$) is a color tone having higher $L^*$ value in two color tones having the longest distance, and $C_2$ ($CL^*_2$, $Ca^*_2$, $Cb^*_2$), $C_3$ ($CL^*_3$, $Ca^*_3$, $Cb^*_3$), to $C_{n-1}$, ($CL^*_{n-1}$, $Ca^*_{n-1}$, $Cb^*_{n-1}$), Cn ($CL^*_n$, $Ca^*_n$, $Cb^*_n$) are color tones in the order of closer distance from the $C_1$ ($CL^*_1$, $Ca^*_1$, $Cb^*_1$), in the $L^*a^*b^*$ space, each color tone C ($CL^*$, $Ca^*$, $Cb^*$) in the plurality of dental cements having the 3 to n colors satisfies that an amount of information loss Pin in each color tone with regard to first principal component determined by principal component analysis of each of the color tones $C_1$ ($CL^*_1$, $Ca^*_1$, $Cb^*_1$), $C_2$ ($CL^*_2$, $Ca^*_2$, $Cb^*_2$), to $C_{n-1}$, ($CL^*_{n-1}$, $Ca^*_{n-1}$, $Cb^*_{n-1}$), Cn ($CL^*_n$, $Ca^*_n$, $Cb^*_n$) is less than 2, and following Formula 1.

$$2 \le ((CL^*_{p-1} - CL^*_p)^2 + (Ca^*_{p-1} - Ca^*_p)^2 + (Cb^*_{p-1} - Cb^*_p)^2)^{1/2} < 8 \quad \text{Formula 1}$$

(wherein p is an arbitrary integer of $2 \le p \le n$)

In the dental cement set of the present invention, it is preferable that the amount of information loss Pin with regard to the first principal component which is determined by the principal component analysis is less than 1.5.

The dental cement trial test material kit of the present invention is a dental cement trial test material kit consisting of the dental cement set of the present invention and a trial test material set consisting of a plurality of trial test materials corresponding to color tone of each dental cement, wherein, each color tone $T_1$ ($TL^*_1$, $Ta^*_1$, $Tb^*_1$), $T_2$ ($TL^*_2$, $Ta^*_2$, $Tb^*_2$), to $T_{n-1}$, ($TL^*_{n-1}$, $Ta^*_{n-1}$, $Tb^*_{n-1}$), Tn ($TL^*_n$, $Ta^*_n$, $Tb^*_n$) of the trial test materials corresponding to each color tone $C_1$ ($CL^*_1$, $Ca^*_1$, $Cb^*_1$) $C_2$ ($CL^*_2$, $Ca^*_2$, $Cb^*_2$), to $C_{n-1}$, ($CL^*_{n-1}$, $Ca^*_{n-1}$, $Cb^*_{n-1}$), Cn ($CL^*_n$, $Ca^*_n$, $Cb^*_n$) of the dental cements having the 3 to n colors in $L^*a^*b^*$ space satisfies following Formula 2.

$$0 \le ((CL^*_p - TL^*_p)^2 + (Ca^*_p - Ta^*_p)^2 + (Cb^*_p - Tb^*_p)^2)^{1/2} \le 2, \text{ and } 0 \le ((CL^*_1 - TL^*_1)^2 + (Ca^*_1 - Ta^*_1)^2 + (Cb^*_1 - Tb^*_1)^2)^{1/2} \le 2 \quad \text{Formula 2}$$

(wherein p is an arbitrary integer of $2 \le p \le n$).

The dental cement selection method of the present invention is a dental cement selection method selecting a dental cement to be used from a plurality of dental cements having color tones of 3 to n colors after trial test with a plurality of trial test materials corresponding to the color tones of the 3 to n colors, wherein the method uses a dental cement trial test material kit comprising a dental cement set and a trial test material set, wherein:

the dental cement set consisting of a plurality of dental cements having color tones of 3 to n colors, wherein when it is defined that $C_1$ ($CL^*_1$, $Ca^*_1$, $Cb^*_1$) is a color tone having higher $L^*$ value in two color tones having the longest distance, and $C_2$ ($CL^*_2$, $Ca^*_2$, $Cb^*_2$), $C_3$ ($CL^*_3$, $Ca^*_3$, $Cb^*_3$), to $C_{n-1}$, ($CL^*_{n-1}$, $Ca^*_{n-1}$, $Cb^*_{n-1}$), Cn ($CL^*_n$, $Ca^*_n$, $Cb^*_n$) are color tones in the order of closer distance from the $C_1$ ($CL^*_1$, $Ca^*_1$, $Cb^*_1$), in the $L^*a^*b^*$ space, each color tone C ($CL^*$, $Ca^*$, $Cb^*$) in the plurality of dental cements having the 3 to n colors satisfies that an amount of information loss Pln in each color tone with regard to first principal component determined by principal component analysis of each of the color tones $C_1$ ($CL^*_1$, $Ca^*_1$, $Cb^*_1$), $C_2$ ($CL^*_2$, $Ca^*_2$, $Cb^*_2$), to $C_{n-1}$, ($CL^*_{n-1}$, $Ca^*_{n-1}$, $Cb^*_{n-1}$), Cn ($CL^*_n$, $Ca^*_n$, $Cb^*_n$) is less than 2, and following Formula 1, $$2 \leq ((CL^*_{p-1}-CL^*_p)^2 + (Ca^*_{p-1}-Ca^*_p)^2 + (Cb^*_{p-1}-Cb^*_p)^2)^{1/2} \leq 8 \quad \text{Formula 1}$$

(wherein p is an arbitrary integer of $2 \leq p \leq n$), and the trial test material set consisting of a plurality of trial test materials corresponding to the color tone of each dental cement, wherein, each color tone $T_1$ ($TL^*_1$, $Ta^*_1$, $Tb^*_1$), $T_2$ ($TL^*_2$, $Ta^*_2$, $Tb^*_2$), to $T_{n-1}$, ($TL^*_{n-1}$, $Ta^*_{n-1}$, $Tb^*_{n-1}$), Tn ($TL^*_n$, $Ta^*_n$, $Tb^*_n$) of the trial test materials corresponding to each color tone of the dental cements having the 3 to n colors satisfies following Formula 2.

$$0 \leq ((CL^*_p-TL^*_p)^2 + (Ca^*_p-Ta^*_p)^2 + (Cb^*_p-Tb^*_p)^2)^{1/2} \leq 2, \text{ and } 0 \leq ((CL^*_1-TL^*_1)^2 + (Ca^*_1-Ta^*_1)^2 + (Cb^*_1-Tb^*_1)^2)^{1/2} \leq 2 \quad \text{Formula 2}$$

(wherein p is an arbitrary integer of $2 \leq p \leq n$).

Advantageous Effects of Invention

In mounting of or trial test of a prosthesis device, it is possible to select a dental cement or a trial test material for easily obtaining high color tone adaptability to peripheral tooth substances.

In using the trial test material of the present invention, as a result of using adjacent trial test materials in the $L^*a^*b^*$ space for changing to a suitable color tone, in case of further changing in the same color direction, it can be approximated to the suitable color tone with sense of change similar to the sense of color tone change by visual observation, by using a trial test material which is adjacent to the used trial test materials.

DETAILED DESCRIPTION OF THE PREFERRED EMBODIMENTS

The present inventors found that the above described problem is caused by that the relationship between color tones in each dental cement and each trial test material is not appropriate, in amending color tone in a portion to be restored.

As a result of intensive studies, it has been found that when the color differences between each pair of color tones are a constant interval and an amount of information loss Pin in each color tone with regard to first principal component determined by principal component analysis of each of the color tones $C_1$ ($CL^*_1$, $Ca^*_1$, $Cb^*_1$), $C_2$ ($CL^*_2$, $Ca^*_2$, $Cb^*_2$), to $C_{n-1}$, ($CL^*_{n-1}$, $Ca^*_{n-1}$, $Cb^*_{n-1}$), Cn ($CL^*_n$, $Ca^*_n$, $Cb^*_n$) is less than 2 in the $L^*a^*b^*$ space, in other word, when color tones of each dental cement and each trial test material linearly exist and each of color tones is positioned at a constant interval in the $L^*a^*b^*$ space, because the same system color is maintained and the color tones are different in a degree such that the color difference can be recognized in mounting of or trial test of a prosthesis device, it is possible to finely adjust brightness and saturation and it is possible to easily obtain high color tone adaptability to peripheral tooth substances.

That is, the dental cement set of the present invention is a dental cement set consisting of a plurality of dental cements having color tones of n colors which is at least 3 colors, wherein when color tone C ($CL^*$, $Ca^*$, $Cb^*$) of each cement is expressed in $L^*a^*b^*$ space and it is defined that $C_1$ ($CL^*_1$, $Ca^*_1$, $Cb^*_1$) is a color tone having higher $L^*$ value in two color tones having the longest distance, and $C_2$ ($CL^*_2$, $Ca^*_2$, $Cb^*_2$), $C_3$ ($CL^*_3$, $Ca^*_3$, $Cb^*_3$) to $C_{n-1}$, ($CL^*_{n-1}$, $Ca^*_{n-1}$, $Cb^*_{n-1}$), Cn ($CL^*_n$, $Ca^*_n$, $Cb^*_n$) are color tones in the order of closer distance from the $C_1$ ($CL^*_1$, $Ca^*_n$, $Cb^*_n$), in the $L^*a^*b^*$ space, an amount of information loss P1n in each color tone with regard to first principal component determined by principal component analysis of each of the color tones $C_1$ ($CL^*_1$, $Ca^*_1$, $Cb^*_1$), $C_2$ ($CL^*_2$, $Ca^*_2$, $Cb^*_2$), to $C_{n-1}$, ($CL^*_{n-1}$, $Ca^*_{n-1}$, $Cb^*_{n-1}$), Cn ($CL^*_n$, $Ca^*_n$, $Cb^*_n$) is less than 2, and the dental cement set satisfies following Formula 1.

$$2 \leq ((CL^*_{p-1}-CL^*_p)^2 + (Ca^*_{p-1}-Ca^*_p)^2 + (Cb^*_{p-1}-Cb^*_p)^2)^{1/2} < 8 \quad \text{Formula 1}$$

(wherein p is an arbitrary integer of $2 \leq p \leq n$)

The $L^*a^*b^*$ space means a space that CIELab color system in accordance with JIS Z8729 is three-dimensionally displayed. In this space, $L^*$ refers brightness, $a^*$ and $b^*$ refer chromaticity indicating hue and saturation (chroma), $L^*$ indicates brightness as the $L^*$ value gets closer to 100 and darkness as the $L^*$ value gets closer to 0, $a^*$ indicates red in + direction and green in − direction, W indicates yellow in + direction and blue in − direction, and saturation becomes higher and colorful as absolute value is large in $a^*$ and $b^*$.

The color tone of the dental cement kit in the embodiment of the present invention is measured in accordance with JIS Z8729. A test specimen of a set dental cement (thickness 0.5 mm) is color measured under white background by SCI method to obtain $L^*$, $a^*$, $b^*$. Similarly, a test specimen of a trial test material (thickness 0.5 mm) is color measured under white background by SCI method to obtain $L^*$, $a^*$, $b^*$. In the present invention, the measured $L^*$, $a^*$, $b^*$ corresponds to the coordinates C ($CL^*$, $Ca^*$, $Cb^*$) or T ($TL^*$, $Ta^*$, $Tb^*$) of each color tone in the $L^*a^*b^*$ space.

Further, it is defined that $C_1$ ($CL^*_1$, $Ca^*_1$, $Cb^*_1$) is a color tone having higher $L^*$ value in two color tones having the longest distance, that is, having the biggest color difference and $C_2$ ($CL^*_2$, $Ca^*_2$, $Cb^*_2$) to $C_{n-1}$, ($CL^*_{n-1}$, $Ca^*_{n-1}$, $Cb^*_{n-1}$), Cn ($CL^*_n$, $Ca^*_n$, $Cb^*_n$) are color tones in the order of closer distance from the $C_1$ ($CL^*_1$, $Ca^*_1$, $Cb^*_1$), in the $L^*a^*b^*$ space.

However, the present invention may include a dental cement or a trial test material having a color tone such as a masking color represented by an opaque which shields metal color. There is a case that they do not follow the above rules.

In the color tones of C ($CL^*$, $Ca^*$, $Cb^*$) of the dental cement and T ($TL^*$, $Ta^*$, $Tb^*$) of the trial test material in the present invention, in order to resemble a wide range of color tones from natural tooth to discolored tooth and tooth after whitening, the $L^*$ value is preferably 50 to 99, more preferably 60 to 98, the $a^*$ value is preferably −5 to 5, more preferably −4 to 4, and the $b^*$ value is preferably −1 to 22, more preferably 0 to 20; and these values are selected from the range described above.

In the present invention, it is necessary to have a certain color difference in a degree such that a color tone of the same system can be recognized and the color difference can be recognized in mounting of or trial test of a prosthesis device, for a distance between $C_{p-1}$ ($CL^*_{p-1}$, $Ca^*_{p-1}$, $Cb^*_{p-1}$) and $C_p$ ($CL^*_p$, $Ca^*_p$, $Cb^*_p$), that is, for a color difference between $C_{p-1}$ ($CL^*_{p-1}$, $Ca^*_{p-1}$, $Cb^*_{p-1}$) and $C_p$ ($CL^*_p$, $Ca^*_p$, $Cb^*_p$) in the $L^*a^*b^*$ space (wherein p is an arbitrary integer of $2 \leq p \leq n$).

When the color difference between $C_{p-1}$ ($CL^*_{p-1}$, $Ca^*_{p-1}$, $Cb^*_{p-1}$) and $C_p$ ($CL^*_p$, $Ca^*_p$, $Cb^*_p$) is less than 2, in mounting of or trial test of a prosthesis device, it may be difficult to visually recognize a color difference between each pair of color tones, and it is recognized that the colors are the same. On the other hand, when the color difference is 8 or more, it is visually recognized that the systems of the color tones are clearly different. Therefore, it is preferable that the color difference between $C_{p-1}$ ($CL^*_{p-1}$, $Ca^*_{p-1}$, $Cb^*_{p-1}$) and $C_p$ ($CL^*_p$, $Ca^*_p$, $Cb^*_p$) is 2 or more and less than 8 (Formula 1). In addition, it is preferable that the color difference between $C_{p-1}$. ($CL^*_{p-1}$, $Ca^*_{p-1}$, $Cb^*_{p-1}$) and $C_p$ ($CL^*_p$, $Ca^*_p$, $Cb^*_p$) is 3 or more and less than 7 (Formula 2), in order to clearly recognize the color difference and to maintain an approximate system of the color tone.

$$2 \leq ((CL^*_{p-1} - CL^*_p)^2 + (Ca^*_{p-1} - Ca^*_p)^2 + (Cb^*_{p-1} - Cb^*_p)^2)^{1/2} < 8 \quad \text{Formula 1}$$

(wherein p is an arbitrary integer of $2 \leq p \leq n$)

$$3 \leq ((CL^*_{p-1} - CL^*_p)^2 + (Ca^*_{p-1} - Ca^*_p)^2 + (Cb^*_{p-1} - Cb^*_p)^2)^{1/2} < 7 \quad \text{Formula 1a}$$

(wherein p is an arbitrary integer of $2 \leq p \leq n$)

Further, it is preferable that a maximum value of an absolute value of a difference between adjacent color tones in the dental cements of 3 to n colors is within 3 or less. It becomes easy to match with an adaptation sense by visual observation. If there is a large variation in a difference between the adjacent color tones in the dental cements of 3 to n colors, it may deviate from an adaptation sense by visual observation.

An explanation of the principal component analysis of each of the color tones $C_1$ ($CL^*_1$, $Ca^*_1$, $Cb^*_1$), $C_2$ ($CL^*_2$, $Ca^*_2$, $Cb^*_2$), to $C_{n-1}$, ($CL^*_{n-1}$, $Ca^*_{n-1}$, $Cb^*_{n-1}$), Cn ($CL^*_n$, $Ca^*_n$, $Cb^*_n$) of the dental cements in $L^*a^*b^*$ space will be described. Principal component analysis is a multivariate analysis method in which the information of N variables is summarized into fewer m total characteristic values, that is, principal components (Z1, Z2, Z3 . . . Zm) (m≤N).

Mathematical 1

The calculation method of an amount of information loss Pmn with regard to first principal component in the present invention is as follows. A variance-covariance matrix of data C ($C_1$, $C_2$, $C_3$, to $C_n$) in $L^*a^*b^*$ space is calculated by using formula (1).

$$S_{ij} = \frac{1}{n-1} \sum_{k=1}^{n} (C_i(k) - \overline{C}_i)(C_j(k) - \overline{C}_j) \quad (1)$$

Eigenvalues ($\lambda_1$, $\lambda_2$, $\lambda_3$) are calculated by using formula (2) from the variance-covariance matrix.

$$\begin{vmatrix} S_{L^*L^*} - \lambda & S_{a^*L^*} & S_{b^*L^*} \\ S_{L^*a^*} & S_{a^*a^*} - \lambda & S_{b^*a^*} \\ S_{L^*b^*} & S_{a^*b^*} & S_{b^*b^*} - \lambda_m \end{vmatrix} = 0 \quad (2)$$

Principal component vectors $Z_1$ ($ZL^*_1$, $Za^*_1$, $Zb^*_1$), $Z_2$ ($ZL^*_2$, $Za^*_2$, $Zb^*_2$) and $Z_3$($ZL^*_3$, $Za^*_3$, $Zb^*_3$) with regard to each eigenvalue are calculated by using formula (3).

$$\begin{pmatrix} S_{L^*L^*} - \lambda_m & S_{a^*L^*} & S_{b^*L^*} \\ S_{L^*a^*} & S_{a^*a^*} - \lambda_m & S_{b^*a^*} \\ S_{L^*b^*} & S_{a^*b^*} & S_{b^*b^*} - \lambda_m \end{pmatrix} \begin{pmatrix} ZL^*_m \\ Za^*_m \\ Zb^*_m \end{pmatrix} = 0 \quad (3)$$

In this case, main component vectors are orthogonal to each other and correlation becomes 0. Dispersion of each main component corresponds to the magnitude of eigenvalue ($\lambda_1$, $\lambda_2$, $\lambda_3$). First principal component, second principal component and third principal component are defined in order of the magnitude of the dispersion (When the color tone is up to $C_3$, only first principal component and second principal component are defined). Straight lines $C_m$ ($CL^*_m$, $Ca^*_m$, $Cb^*_m$) which are the axis of each principal component are expressed by formula (4) using principal component vector $Z_m$ ($ZL^*_m$, $Za^*_m$, $Zb^*_m$), principal component score $Y_{mn}$ and average vector M ($ML^*$, $Ma^*$, $Mb^*$).

$$\begin{pmatrix} CL^*_m \\ Ca^*_m \\ Cb^*_m \end{pmatrix} = Y_{mn} \cdot \begin{pmatrix} ZL^*_m \\ Za^*_m \\ Zb^*_m \end{pmatrix} + \begin{pmatrix} ML^* \\ Ma^* \\ Mb^* \end{pmatrix} \quad (4)$$

Principal component score $Y_{mn}$ means a magnitude of contribution with regard to data point of principal component vector and is expressed by formula (5).

$$\begin{pmatrix} Y_1 n \\ Y_2 n \\ Y_3 n \end{pmatrix} = \begin{pmatrix} ZL^*_1 & Za^*_1 & Zb^*_1 \\ ZL^*_2 & Za^*_2 & Zb^*_2 \\ ZL^*_3 & Za^*_3 & Zb^*_3 \end{pmatrix} \cdot \begin{pmatrix} CL^*n - ML^* \\ Ca^*n - Ma^* \\ Cb^*n - Mb^* \end{pmatrix} \quad (5)$$

An amount of information loss Pmn with regard to first principal component is expressed by formula (6) by principal component score.

$$P_{mn} = \sqrt{(Y_1 n)^2 + (Y_2 n)^2 + (Y_3 n)^2 - (Y_m n)^2} \quad (6)$$

As an amount of information loss Pin with regard to first principal component approaches 0, orthogonal distance between axis of the first principal component of color tone group and each color tone $C_p$ ($CL^*_p$, $Ca^*_p$, $Cb^*_p$) becomes small, which means dispersion becomes small. When an amount of information loss Pin with regard to first principal component is 0, each color tone exist on the same straight line in $L^*a^*b^*$ space.

Figure 1:
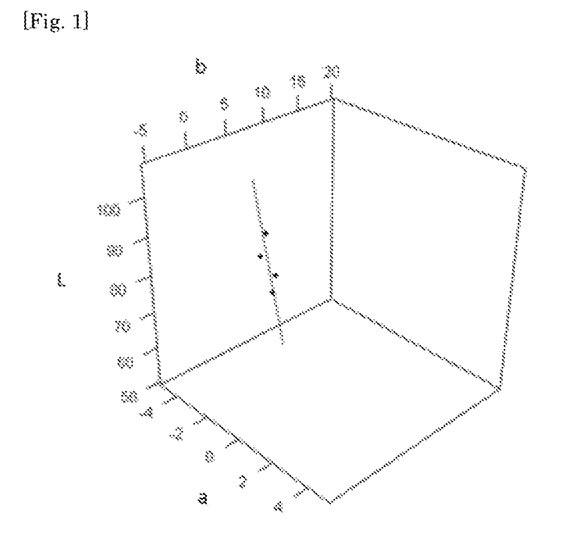
Figure 2:
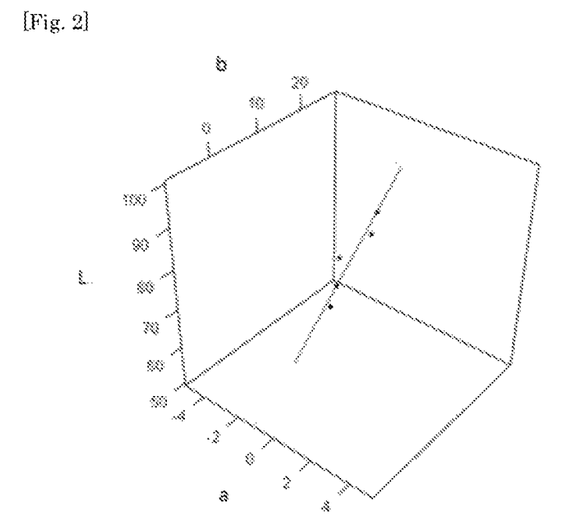
Figure 3:
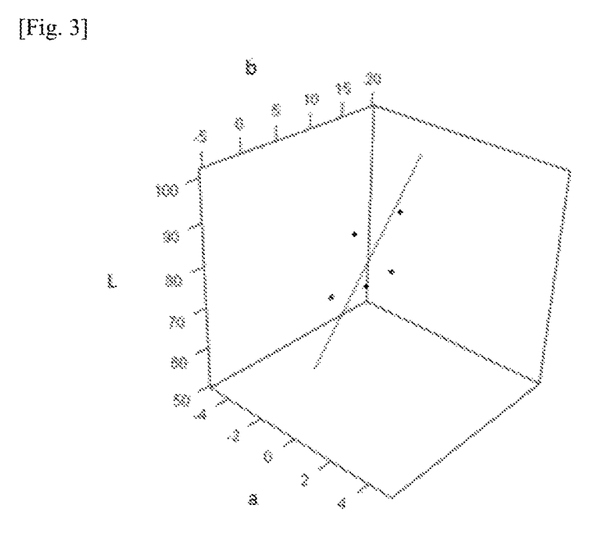

An explanation of the relationship between each color tone and an amount of information loss Pin in each color tone for first principal component in $L^*a^*b^*$ space will be described. In the color tone shown in FIG. 1. (dental cement kit (1) described as a specific example), the first principal component axis is close to the brightness axis, and therefore the dental cement kit can mainly adjust $L^*$. Further, because the dispersion of each color tone from the first principal component axis (amount of information loss: P1n=0.73) is sufficiently small, it is indicated that it has linearity and that a system of the color tone is maintained. In the color tone shown in FIG. 2 (dental cement kit (4) described as a specific example), the first principal component axis is related to $L^*$ and $b^*$, therefore it is possible to adjust $L^*$ and $b^*$ simultaneously. In addition, as in FIG. 1, because the dispersion of each color tone from the first principal component axis (amount of information loss: P1n=1.81) is small, it is indicated that it has linearity and that a system of the color tone is maintained. On the other hand, in the color tone shown in FIG. 3 (dental cement kit (9) described as a specific example), although the first principal component axis is related to $L^*$ and $b^*$, the dispersion of each color tone from the first principal component axis (amount of information loss: P1n=3.23) is large, therefore it is indicated that it does not have linearity, that is, $L^*$ and $b^*$ are scattered, and that a system of the color tone is not maintained.

Each of the color tones consisting of $C_1$ ($CL^*_1$, $Ca^*_1$, $Cb^*_1$), $C_2$ ($CL^*_2$, $Ca^*_2$, $Cb^*_2$), to $C_{n-1}$ ($CL^*_{n-1}$, $Ca^*_{n-1}$, $Cb^*_{n-1}$) $Cn$ ($CL^*_n$, $Ca^*_n$, $Cb^*_n$) linearly exists in the $L^*a^*b^*$ space. Specifically, an amount of information loss P1n in each color tone with regard to first principal component determined by principal component analysis is less than 2, and preferably less than 1.5. When the amount of information loss P1n is 2 or more, each color tone disperses in $L^*a^*b^*$ space, therefore, a fine adjustment of brightness and saturation may be difficult in mounting of or trial test of a prosthesis device. When the amount of information loss P1n is less than 2, the linearity is maintained, therefore, a fine adjustment of brightness and saturation may be easy.

The dental cement of the present invention may be used in any property and form without any limitation, and may be paste type or powder-liquid type. With respect to paste type cement, it may be 1 paste type or 2 paste type.

The kit of the present invention may contain a trial test material in addition to a dental cement. The trial test material must have a color tone close to that of the dental cement after setting in order to reproduce a color tone of a portion to be restored or a tooth to be restored which are mounted with a prosthesis device by using the dental cement. Therefore, a color difference between color tone C ($CL^*$, $Ca^*$, $Cb^*$) of each cement and color tone T ($TL^*$, $Ta^*$, $Tb^*$) of a trial test material corresponding to the cement is preferably less than 2 (Formula 2) and more preferably less than 1.5 (Formula 2a). When a color difference between color tone C ($CL^*$, $Ca^*$, $Cb^*$) of each cement and color tone T ($TL^*$, $Ta^*$, $Tb^*$) of a trial test material corresponding to the cement is 2 or more, a difference is confirmed in color tone between a trial test material and a dental cement, and it is difficult in a trial test to reproduce a color tone after mounting a prosthesis device.

$$0 \le ((CL^*_p - TL^*_p)^2 + (Ca^*_p - Ta^*_p)^2 + (Cb^*_p - Tb^*_p)^2)^{1/2} \le 2, \text{ and } 0 \le ((CL^*_1 - TL^*_1)^2 + (Ca^*_1 - Ta^*_1)^2 + (Cb^*_1 - Tb^*_1)^2)^{1/2} \le 2 \quad \text{Formula 2}$$

(wherein p is an arbitrary integer of $2 \le p \le n$).

$$0 \le ((CL^*_p - TL^*_p)^2 + (Ca^*_p - Ta^*_p)^2 + (Cb^*_p - Tb^*_p)^2)^{1/2} \le 1.5, \text{ and } 0 \le ((CL^*_1 - TL^*_1)^2 + (Ca^*_1 - Ta^*_1)^2 + (Cb^*_1 - Tb^*_1)^2)^{1/2} \le 1.5 \quad \text{Formula 2a}$$

(wherein p is an arbitrary integer of $2 \le p \le n$).

A kit of the dental cement of the present invention may contain a dental primer, a dental dentin adhesive material, a dental etching material, a shade guide and an oxygen blocking material in addition to the dental cement and the trial test material. The present invention is described specifically with reference to Examples. However, the present invention is not limited to Examples.

EXAMPLES

Color Tone Measurement of Dental Cement

A polyacetal mold having a hole (diameter 15 mm, height 0.5 mm) was placed on a glass plate (thickness 0.15±0.02 mm), and a dental cement was filled in the hole. Then, the upper part was pressure-contacted with another glass plate (thickness 0.15±0.02 mm), and it was confirmed that there are no air bubbles. Thereafter, light was irradiated to both sides with a LED irradiator (Blue Shot High Mode: manufactured by Shofu Inc.) for 20 seconds by 9 times. After the light irradiation, it was confirmed that the surfaces of the dental cement material and the glass plates did not peel off, and the color was measured by a SCI method under a white background using a colorimeter (CM-3500d: manufactured by Konica Minolta, Inc.). Color Tone Measurement of Trial Test Material.

A polyacetal mold having a hole (diameter 15 mm, height 0.5 mm) was placed on a glass plate (thickness 0.15±0.02 mm), and a trial test material was filled in the hole. Then, the upper part was pressure-contacted with another glass plate (thickness 0.15±0.02 mm), and it was confirmed that there are no air bubbles. Thereafter, the color was measured by a SCI method under a white background using a colorimeter (CM-3500d: manufactured by Konica Minolta, Inc.).

TABLE 1

| | $L^*$ | $a^*$ | $b^*$ | Suitability for Formula (1) | Color difference $\Delta E$ | Amount of information loss P1n |
|---|---|---|---|---|---|---|
| Dental cement kit (1) | | | | | | |
| $C_1$ | 94.42 | −1.11 | 1.23 | | | 0.39 |
| $C_2$ | 89.74 | −0.99 | 0.21 | ○ | 4.79 | 0.73 |
| $C_3$ | 84.64 | −0.67 | 1.39 | ○ | 5.24 | 0.37 |
| $C_4$ | 80.29 | −0.74 | 1.14 | ○ | 4.36 | 0.08 |
| Dental cement kit (2) | | | | | | |
| $C_1$ | 90.18 | 0.75 | 11.22 | | | 0.65 |
| $C_2$ | 88.82 | 0.99 | 7.64 | ○ | 3.84 | 1.02 |
| $C_3$ | 83.05 | 0.84 | 4.23 | ○ | 6.70 | 0.96 |
| $C_4$ | 81.15 | −0.69 | 0.94 | ○ | 4.10 | 0.58 |
| Dental cement kit (3) | | | | | | |
| $C_1$ | 84.64 | −0.67 | 1.39 | | | 0.57 |
| $C_2$ | 85.98 | 0.88 | 5.55 | ○ | 4.64 | 1.55 |
| $C_3$ | 82.13 | −0.43 | 10.84 | ○ | 6.67 | 1.73 |
| $C_4$ | 83.22 | 0.23 | 16.75 | ○ | 6.05 | 0.76 |
| Dental cement kit (4) | | | | | | |
| $C_1$ | 84.64 | −0.67 | 18.93 | | | 0.09 |
| $C_2$ | 83.45 | −0.02 | 14.42 | ○ | 4.71 | 1.00 |
| $C_3$ | 78.75 | −0.83 | 10.42 | ○ | 6.22 | 1.81 |
| $C_4$ | 78.07 | 0.23 | 5.01 | ○ | 5.55 | 0.02 |
| $C_5$ | 77.07 | 0.74 | 1.39 | ○ | 3.79 | 0.71 |

TABLE 2

| | $L^*$ | $a^*$ | $b^*$ | Suitability for Formula (1) | Color difference $\Delta E$ | Amount of information loss P1n |
|---|---|---|---|---|---|---|
| Dental cement kit (5) | | | | | | |
| $C_1$ | 80.29 | 0.75 | 13.84 | | | 0.29 |
| $C_2$ | 83.74 | 0.99 | 10.24 | ○ | 4.99 | 0.83 |
| $C_3$ | 85.04 | 0.84 | 4.21 | ○ | 6.17 | 0.93 |
| $C_4$ | 88.33 | 1.31 | 0.38 | ○ | 5.07 | 0.39 |

TABLE 2-continued

|  | L* | a* | b* | Suitability for Formula (1) | Color difference ⊿E | Amount of information loss P1n |
|---|---|---|---|---|---|---|
| Dental cement kit (6) | | | | | | |
| C₁ | 93.74 | 0.99 | 4.99 | | | 0.39 |
| C₂ | 89.98 | −0.28 | 4.01 | ○ | 4.09 | 0.67 |
| C₃ | 86.32 | 0.01 | 3.87 | ○ | 3.67 | 0.65 |
| C₄ | 82.81 | 0.63 | 2.23 | ○ | 3.92 | 0.77 |
| C₅ | 79.45 | −0.74 | 1.14 | ○ | 3.79 | 0.43 |
| Dental cement kit (7) | | | | | | |
| C₁ | 94.42 | −1.11 | 1.23 | | | 0.06 |
| C₂ | 84.64 | −0.67 | 1.39 | x | 9.79 | 0.18 |
| C₃ | 80.29 | −0.74 | 1.14 | ○ | 4.36 | 0.13 |
| Dental cement kit (8) | | | | | | |
| C₁ | 83.22 | 0.23 | 16.75 | | | 0.16 |
| C₂ | 82.94 | 0.11 | 13.63 | ○ | 3.13 | 0.54 |
| C₃ | 85.98 | −0.38 | 5.55 | x | 8.65 | 2.20 |
| C₄ | 82.48 | 0.23 | 1.43 | ○ | 5.44 | 1.52 |

TABLE 3

|  | L* | a* | b* | Suitability for Formula (1) | Color difference ⊿E | Amount of information loss P1n |
|---|---|---|---|---|---|---|
| Dental cement kit (9) | | | | | | |
| C₁ | 90.23 | −0.21 | 10.48 | | | 1.63 |
| C₂ | 88.00 | −0.74 | 5.04 | ○ | 5.90 | 2.42 |
| C₃ | 83.04 | 1.21 | 5.11 | ○ | 5.33 | 1.25 |
| C₄ | 76.21 | −0.22 | 5.58 | ○ | 6.99 | 3.23 |
| C₅ | 78.21 | −0.22 | 0.32 | ○ | 5.63 | 2.40 |
| Dental cement kit (10) | | | | | | |
| C₁ | 84.64 | −0.67 | 1.39 | | | 0.21 |
| C₂ | 84.02 | −0.76 | 0.98 | x | 0.75 | 0.22 |
| C₃ | 82.96 | −0.99 | 1.21 | x | 1.11 | 0.22 |
| C₄ | 81.92 | −0.74 | 1.14 | x | 1.07 | 0.07 |
| C₅ | 80.98 | −0.67 | 1.39 | x | 0.98 | 0.19 |
| C₆ | 80.29 | −0.74 | 1.14 | x | 0.74 | 0.08 |
| Dental cement kit (11) | | | | | | |
| C₁ | 84.76 | −0.97 | 1.45 | | | 0.85 |
| C₂ | 80.29 | −0.74 | 1.14 | ○ | 4.49 | 2.44 |
| C₃ | 83.98 | −0.38 | 5.55 | ○ | 5.76 | 2.88 |
| C₄ | 76.98 | −0.22 | 7.22 | ○ | 7.20 | 2.42 |
| C₅ | 76.08 | −0.22 | 2.87 | ○ | 4.44 | 2.00 |

TABLE 4

|  | L* | a* | b* | Color difference between dental cement kit (1) ⊿E |
|---|---|---|---|---|
| Trial test material kit (1) (Colorimetry to Dental cement kit (1)) | | | | |
| T₁ | 93.99 | −0.88 | 0.87 | 0.61 |
| T₂ | 90.02 | −1.43 | 0.72 | 0.73 |
| T₃ | 85.01 | −0.98 | 0.58 | 0.94 |
| T₄ | 80.57 | −0.21 | 0.77 | 0.70 |
| Trial test material kit (2) (Colorimetry to Dental cement kit (1)) | | | | |
| T₁ | 92.75 | −0.76 | 0.66 | 1.80 |
| T₂ | 88.13 | −1.50 | 0.00 | 1.70 |
| T₃ | 84.85 | −1.03 | 0.43 | 1.05 |
| T₄ | 79.87 | −0.44 | 0.54 | 0.79 |
| Trial test material kit (3) (Colorimetry to Dental cement kit (1)) | | | | |
| T₁ | 91.23 | −0.99 | 1.11 | 3.20 |
| T₂ | 87.53 | −1.42 | 0.44 | 2.26 |
| T₃ | 85.02 | −2.21 | 4.22 | 3.24 |
| T₄ | 80.25 | −4.03 | 0.88 | 3.30 |

Evaluation Method of Color Tone Adjustability

After taking an impression body of a shade guide (VITA-PAN Classical A1, A2 or A3: manufactured by VITA Zahnfabrik H. Rauter GmbH & Co.KG) by an impression material (SILDEFIT: manufactured by Shofu Inc.), an enamel layer of the shade guide was removed with an abrasive. A surface after removal was ground by water-resistant abrasive paper No, 600 and No. 2000 in the order, to prepare an abutment tooth model. Next, after attaching a heat-resistant film having a thickness of 50 μm to the abutment tooth model, a composite resin (BEAUTIFIL Flow Plus F03 A1 and A3 colors: manufactured by Shofu Inc.) was laminated on the part corresponding to the enamel layer. Then, the impression body was pressure-contacted from the labial surface side, and light was irradiated to prepare a laminate veneer model.

A small amount of dental cement was applied on the laminate veneer model, pressure-contacted with the abutment tooth model, and irradiated with light for 20 seconds using an LED irradiator (Blue Shot High Mode: manufactured by Shofu Inc.) to prepare a restoration model. A restoration model using each color tone of the dental cement was prepared, and the color tone adjustability of the dental cement was evaluated by visual colorimetry with a shade guide.

AA: The color tone of the restoration part was easily adjusted, and high color tone adaptability with the shade guide can be easily obtained.

A: The color tone of the restoration part was easily adjusted, and high color tone adaptability with the shade guide can be obtained.

$x_a$: The color difference between the color tones was so large and the color tone of the restoration area could not be adjusted.

$x_b$: The color difference between the color tones could not be visually recognized and the color tone of the restoration area could not be adjusted.

$x_c$: The system of the color tone of the restoration part was extremely different and the color tone of the restoration area could not be adjusted.

TABLE 5

| | | Used shade guide | Suitability for Formula (1) | Suitability for amount of information loss Pin | Color tone adjustability (Selected clor tone) |
|---|---|---|---|---|---|
| Dental cement kit (1) | Example 1 | A1 | ○ | ○: 0.73 | AA ($C_3$) |
| Dental cement kit (2) | Example 2 | A2 | ○ | ○: 1.02 | AA ($C_3$) |
| Dental cement kit (3) | Example 3 | A3 | ○ | ○: 1.73 | A ($C_4$) |
| Dental cement kit (4) | Example 4 | A3 | ○ | ○: 1.81 | A ($C_2$) |
| Dental cement kit (5) | Example 5 | A2 | ○ | ○: 0.93 | AA ($C_3$) |
| Dental cement kit (6) | Example 6 | A2 | ○ | ○: 0.77 | AA ($C_3$) |
| Dental cement kit (7) | Comparative Example 1 | A1 | x | ○: 0.18 | $x_a$ (—) |
| Dental cement kit (8) | Comparative Example 2 | A3 | x | x: 2.20 | $x_a$ (—) |
| Dental cement kit (9) | Comparative Example 3 | A2 | ○ | x: 3.23 | $x_c$ (—) |
| Dental cement kit (10) | Comparative Example 4 | A2 | x | ○: 0.22 | $x_b$ (—) |
| Dental cement kit (11) | Comparative Example 5 | A2 | ○ | x: 2.88 | $x_c$ (—) |

In the dental cement kits (1), (2), (5), and (6), because color difference between each pair of color tones was felt moderately and the color tones were in the same system, it was possible to finely adjust brightness and saturation and it was possible to easily obtain high color tone adaptability to peripheral tooth substances. In the dental cement kits (3) and (4), because color difference between each pair of color tones was felt moderately and the color tones were in the substantially same system, it was possible to finely adjust brightness and saturation and it was possible to obtain high color tone adaptability to peripheral tooth substances. On the other hand, in the dental cement kit (7), the color difference between each pair of color tones was dispersed, and it was difficult to finely adjust the brightness and the saturation. In the dental cement kit (8), because the color difference between each pair of color tones was dispersed and the color system of each color tone was greatly different, it was difficult to obtain color tone adaptability to peripheral tooth substances. Although the dental cement kits (9) and (11) can appropriately recognize the color difference between each pair of color tones, because the color system of each color tone was different, it was difficult to obtain color tone adaptability to peripheral tooth substances. In the dental cement kit (10), each color tone was similar and color difference could not be recognized, and it was impossible to finely adjust brightness and saturation.

As described above, when the color difference between each pair of color tones is moderate and an amount of information loss in each color tone with regard to the axis of the first principal component determined by principal component analysis of each of the color tones is small, it is possible to finely adjust brightness and saturation and it is possible to obtain high color tone adaptability to peripheral tooth substances.

Color Tone Identity Between Dental Cement and Trial Test Material

A small amount of trial test material was applied on a laminate veneer model and pressure-contacted onto the abutment tooth model to prepare a trial model. The color tone identity of the restoration model and the trial model corresponding to each color was evaluated visually.

○: No color difference was observed between the restoration model and the trial model, and the same color can be recognized.

Δ: Although a slight color difference was observed between the restoration model and the trial model, they can be recognized as almost the same color.

X: Color difference was observed between the restoration model and the trial model, and they were recognized as different color tones.

TABLE 6

| | Trial test material kit, Dental cement kit and name of color tone used or evaluation | | | Color difference between dental cement Cn and trial test material Tn ΔE | Color tone identity |
|---|---|---|---|---|---|
| Example 7 | Trial test material kit (1) | Dental cement kit (1) | $C_1$-$T_1$ | 0.61 | ○ |
| Example 8 | | | $C_2$-$T_2$ | 0.73 | ○ |
| Example 9 | | | $C_3$-$T_3$ | 0.94 | ○ |
| Example 10 | | | $C_4$-$T_4$ | 0.7 | ○ |
| Comparative Example 6 | Trial test material kit (2) | Dental cement kit (2) | $C_1$-$T_1$ | 1.8 | Δ |
| Comparative Example 7 | | | $C_2$-$T_2$ | 1.7 | Δ |
| Example 11 | | | $C_3$-$T_3$ | 1.05 | ○ |
| Example 12 | | | $C_4$-$T_4$ | 0.79 | ○ |

TABLE 6-continued

| | Trial test material kit, Dental cement kit and name of color tone used or evaluation | | Color difference between dental cement Cn and trial test material Tn ΔE | Color tone identity |
|---|---|---|---|---|
| Comparative Example 8 | Trial test material kit (3) | Dental cement kit (3) | $C_1$-$T_1$   3.2 | x |
| Comparative Example 9 | | | $C_2$-$T_2$   2.26 | x |
| Comparative Example 10 | | | $C_3$-$T_3$   3.24 | x |
| Comparative Example 11 | | | $C_4$-$T_4$   3.3 | x |

Color difference Was not visually recognized in the restoration model and the trial model using the trial test material kit (1) and the dental cement kit (1) respectively and therefore they were determined to have the same color tone. In the restoration model and trial model using the trial test material kit (2) and the dental cement kit (1) respectively, $C_3$-$T_3$ and $C_3$-$T_4$ could be recognized as the same color. Although the color difference was slightly recognized, $C_1$-$T_1$ and $C_2$-$T_2$ could be recognized as the substantially same color. Both the restoration model and the trial model using the trial test material kit (3) and the dental cement kit (1) respectively, a color difference was recognized and they were not recognized to have the same color tone.

BRIEF DESCRIPTION OF DRAWINGS

FIG. 1

In the color tone shown in FIG. 1 (dental cement kit (1) described as a specific example), the first principal component axis is close to the brightness axis, and therefore the dental cement kit can mainly adjust L*. Further, because the dispersion of each color tone from the first principal component axis (amount of information loss: P1n=0.73) is sufficiently small, it is indicated that it has linearity and that a system of the color tone is maintained.

FIG. 2

In the color tone shown in FIG. 2 (dental cement kit (4) described as a specific example), the first principal component axis is related to L* and b*, therefore it is possible to adjust L* and b* simultaneously. In addition, as in FIG. 1, because the dispersion of each color tone from the first principal component axis (amount of information loss: P1n=1.81) is small, it is indicated that it has linearity and that a system of the color tone is maintained.

FIG. 3

In the color tone shown in FIG. 3 (dental cement kit (9) described as a specific example), although the first principal component axis is related to L* and b*, the dispersion of each color tone from the first principal component axis (amount of information loss: P1n=3.23) is large, therefore it is indicated that it does not have linearity, that is, L* and b* are scattered, and that a system of the color tone is not maintained.

INDUSTRIAL APPLICABILITY

In the dental field, it is available for the cement and trial test material industries.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

What is claimed is:

1. A dental cement set consisting of a plurality of dental cements having color tones including color tones of 3 to n colors for selecting and using a dental cement from the plurality of dental cements having the color tones including the color tones of the 3 to n colors after trial test with trial test materials for the dental cement to be used from the plurality of dental cements having the color tones including the color tones of the 3 to n colors, wherein:

when it is defined that $C_1$ ($CL^*_1$, $Ca^*_1$, $Cb^*_1$) is a color tone having higher L* value in two color tones having the longest distance, and $C_2$ ($CL^*_2$, $Ca^*_2$, $Cb^*_2$), $C_3$ ($CL^*_3$, $Ca^*_3$, $Cb^*_3$), to $C_{n-1}$, ($CL^*_{n-1}$, $Ca^*_{n-1}$, $Cb^*_{n-1}$), Cn ($CL^*_n$, $Ca^*_n$, $Cb^*_n$) are color tones in the order of closer distance from the $C_1$ ($CL^*_1$, $Ca^*_1$, $Cb^*_1$), in the L*a*b* space, each color tone C (CL*, Ca*, Cb*) in the plurality of dental cements having the 3 to n colors satisfies that an amount of information loss Pin in each color tone with regard to first principal component determined by principal component analysis of each of the color tones $C_1$ ($CL^*_1$, $Ca^*_1$, $Cb^*_1$), $C_2$ ($CL^*_2$, $Ca^*_2$, $Cb^*_2$), to $C_{n-1}$, ($CL^*_{n-1}$, $Ca^*_{n-1}$, $Cb^*_{n-1}$), Cn ($CL^*_n$, $Ca^*_n$, $Cb^*_n$) is less than 2, and following Formula 1, $$2 \leq ((CL^*_{p-1}-CL_p)^2+(Ca^*_{p-1}-Ca^*_p)^2+(Cb^*_{p-1}-Cb^*_p)^2)^{1/2} \leq 8 \quad \text{Formula 1}$$

(wherein p is an arbitrary integer of $2 \leq p \leq n$).

2. The dental cement set of claim 1, wherein:

the amount of information loss Pin with the regard to first principal component determined by principal component analysis is less than 1.5.

3. A dental cement trial test material kit comprising the dental cement set of claim 1 and a trial test material set consisting of a plurality of trial test materials corresponding to the color tone of each dental cement, wherein:

each color tone $T_1$ ($TL^*_1$, $Ta^*_1$, $Tb^*_1$), $T_2$ ($TL^*_2$, $Ta^*_2$, $Tb^*_2$), to $T_{n-1}$ ($TL^*_{n-1}$, $Ta^*_{n-1}$, $Tb^*_{n-1}$), $Tn$ ($TL^*_n$, $Ta^*_n$, $Tb^*_n$) of the trial test materials corresponding to each color tone $C_1$ ($CL^*_1$, $Ca^*_1$, $Cb^*_1$), $C_2$ ($CL^*_2$, $Ca^*_2$, $Cb^*_2$), to $C_{n-1}$ ($CL^*_{n-1}$, $Ca^*_{n-1}$, $Cb^*_{n-1}$) $Cn$ ($CL^*_n$, $Ca^*_n$, $Cb^*_n$) of the dental cements having the 3 to n colors in $L^*a^*b^*$ space satisfies following Formula 2, $$0 \leq ((CL^*_p - TL^*_p)^2 + (Ca^*_p - Ta^*_p)^2 + (Cb^*_p - Tb^*_p)^2)^{1/2} \leq 2, \text{ and } 0 \leq ((CL^*_1 - TL^*_1)^2 + (Ca^*_1 - Ta^*_1)^2 + (Cb_1 - Tb^*_1)^2)^{1/2} \leq 2 \quad \text{Formula 2}$$

(wherein p is an arbitrary integer of $2 \leq p \leq n$).

4. A dental cement selection method selecting a dental cement to be used from a plurality of dental cements having color tones including color tones of 3 to n colors after trial test with a plurality of trial test materials including trial test materials corresponding to the color tones of the 3 to n colors, wherein the method uses a dental cement trial test material kit comprising a dental cement set and a trial test material set, wherein:

the dental cement set consisting of a plurality of dental cements having color tones including color tones of 3 to n colors, wherein when it is defined that $C_1$ ($CL^*_1$, $Ca^*_1$, $Cb^*_1$) is a color tone having higher $L^*$ value in two color tones having the longest distance, and $C_2$ ($CL^*_2$, $Ca^*_2$, $Cb^*_2$), $C_3$ ($CL^*_3$, $Ca^*_3$, $Cb^*_3$), to $C_{n-1}$ ($CL^*_{n-1}$, $Ca^*_{n-1}$, $Cb^*_{n-1}$), $Cn$ ($CL^*_n$, $Ca^*_n$, $Cb^*_n$) are color tones in the order of closer distance from the $C_1$ ($CL^*_1$, $Ca^*_1$, $Cb^*_1$), in the $L^*a^*b^*$ space, each color tone C ($CL^*$, $Ca^*$, $Cb^*$) in the plurality of dental cements having the 3 to n colors satisfies that an amount of information loss Pin in each color tone with regard to first principal component determined by principal component analysis of each of the color tones $C_1$ ($CL^*_1$, $Ca^*_1$, $Cb^*_1$), $C_2$ ($CL^*_2$, $Ca^*_2$, $Cb^*_2$), to $C_{n-1}$, ($CL^*_{n-1}$, $Ca^*_{n-1}$, $Cb^*_{n-1}$), $Cn$ ($CL^*_n$, $Ca^*_n$, $Cb^*_n$) is less than 2, and following Formula 1, $$2 \leq ((CL^*_{p-1} - CL^*_p)^2 + (Ca^*_{p-1} - Ca^*_p)^2 + (Cb^*_{p-1} - Cb^*_p)^2)^{1/2} < 8 \quad \text{Formula 1}$$

(wherein p is an arbitrary integer of $2 \leq p \leq n$), and the trial test material set consisting of a plurality of trial test materials corresponding to the color tone of each dental cement, wherein, each color tone $T_1$ ($TL^*_1$, $Ta^*_1$, $Tb^*_1$), $T_2$ ($TL^*_2$, $Ta^*_2$, $Tb^*_2$), to $T_{n-1}$, ($TL^*_{n-1}$, $Ta^*_{n-1}$, $Tb^*_{n-1}$), $Tn$ ($TL^*_n$, $Ta^*_n$, $Tb^*_n$) of the trial test materials corresponding to each color tone of the dental cements having the 3 to n colors satisfies following Formula 2, $$0 \leq ((CL^*_p - TL^*_p)^2 + (Ca^*_p - Ta^*_p)^2 + (Cb^*_p - Tb^*_p)^2)^{1/2} \leq 2, \text{ and } 0 \leq ((CL^*_1 - TL^*_1)^2 + (Ca^*_1 - Ta^*_1)^2 + (Cb^*_1 - Tb^*_1)^2)^{1/2} \leq 2 \quad \text{Formula 2}$$

(wherein p is an arbitrary integer of $2 \leq p \leq n$).

5. The dental cement set of claim 1, wherein the dental cement set consists of the plurality of dental cements having the color tones of 3 to n colors.

6. The dental cement set of claim 2, wherein the dental cement set consists of the plurality of dental cements having the color tones of 3 to n colors.

7. The dental cement trial test material kit of claim 3, wherein the dental cement set consists of the plurality of dental cements having the color tones of 3 to n colors.

8. The dental cement selection method of claim 4, wherein the dental cement set consists of the plurality of dental cements having the color tones of 3 to n colors.

* * * * *